(12) United States Patent
Sharifi et al.

(10) Patent No.: US 9,133,479 B2
(45) Date of Patent: Sep. 15, 2015

(54) EFFECTIVE VECTOR PLATFORM FOR GENE TRANSFER AND GENE THERAPY

(75) Inventors: Behrooz Sharifi, Woodland Hills, CA (US); Prediman K. Shah, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 13/375,285

(22) PCT Filed: Jun. 3, 2010

(86) PCT No.: PCT/US2010/037239
§ 371 (c)(1),
(2), (4) Date: Nov. 30, 2011

(87) PCT Pub. No.: WO2010/141706
PCT Pub. Date: Dec. 9, 2010

(65) Prior Publication Data
US 2012/0070899 A1 Mar. 22, 2012

Related U.S. Application Data

(60) Provisional application No. 61/183,862, filed on Jun. 3, 2009.

(51) Int. Cl.
*C12N 15/86* (2006.01)
*C07K 14/005* (2006.01)

(52) U.S. Cl.
CPC .............. *C12N 15/86* (2013.01); *C07K 14/005* (2013.01); *C12N 2750/14122* (2013.01); *C12N 2750/14143* (2013.01); *C12N 2830/50* (2013.01)

(58) Field of Classification Search
CPC ...... C12N 15/86; C12N 7/00; C12N 2800/22; C12N 2710/16142; C12N 2710/16442; C12N 2710/16622; C12N 2750/14011; C12N 2810/50; C12N 2810/858; C12Q 1/70
See application file for complete search history.

(56) References Cited

U.S. PATENT DOCUMENTS

| | | | |
|---|---|---|---|
| 6,156,303 A * | 12/2000 | Russell et al. | 424/93.2 |
| 6,855,314 B1 * | 2/2005 | Chiorini et al. | 424/93.2 |
| 7,906,111 B2 * | 3/2011 | Wilson et al. | 424/93.2 |
| 2002/0192823 A1 | 12/2002 | Bartlett | |
| 2007/0202081 A1 | 8/2007 | Shah et al. | |

FOREIGN PATENT DOCUMENTS

| | | | |
|---|---|---|---|
| EP | 1732383 A2 | | 12/2006 |
| JP | 2007531537 A | | 11/2007 |
| WO | WO2005033321 | * | 4/2005 |
| WO | 2005097206 A2 | | 10/2005 |
| WO | 2010141706 A1 | | 12/2010 |

OTHER PUBLICATIONS

Wu et al. J. Virol. 2006, vol. 80, No. 22, pp. 11393-11397.*
Miki et al. J. Biologi. Chemist. 1999, vol. 274, No. 41, pp. 29057-29062.*
PCT/US 2010/037239 International Search Report dated Aug. 13, 2010.
PCT/US 2010/037239 Written Opinion dated Aug. 13, 2010.
PCT/US 2010/037239 International Preliminary Report on Patentability dated Dec. 6, 2011.
Cardozo et al. The SCF Ubiquitin Ligase: Insights into a Molecular Machine. Molecular Cell Biology (2004). 5:739-751.
Grimm et al. From Virus Evolution to Vector Revolution: Use of Naturally Occuring Serotypes of Adeno-Associated Virus (AAV) as Novel Vectors for Human Gene Therapy. Current Gene Therapy (2003). 3(4):281-304.
Kanemori et al. B-TrCP Recognizes a Previously Undescribed Nonphosphorylated Destruction Motif in Cdc25A and Cdc25B Phosphatases. PNAS (2005). 102(18):6279-6284.
Orford et al. Serine Phosphorylation-regulated Ubiquitination and Degradation of B-Catenin. The Journal of Biological Chemistry (1997). 272(40): 24735-24738.
Yan et al. Ubiquitination of both Adeno-Associated Virus Type 2 and 5 Capsid Proteins Affects the Transduction Efficiency of Recombinant Vectors. Journal of Virology (2002). 76(5): 2043-2053.
Zhong et al. Next Generation of Adeno-Associated Virus 2 Vectors: Point Mutations in Tyrosines Lead to High-Efficiency Transduction at Lower Doses. PNAS (2008). 105(22): 7827-7832.

* cited by examiner

*Primary Examiner* — Bao Li

(74) *Attorney, Agent, or Firm* — Seth D. Levy; Nixon Peabody LLP

(57) ABSTRACT

The invention relates to the discovery that mutations of serine residues of an AAV capsid results in significantly greater transfection efficiency than the wild type AAV2 virus. In one embodiment, the present invention provides a method of improving efficiency of gene transfer and/or gene therapy to a cell by inhibiting phosphorylation of one or more serine residues of a virus capsid protein, where the inhibition of the phosphorylation of one or more serine residues results in a decrease of ubiquitination of the virus capsid protein in the cell. In another embodiment, one of the one or more serine residues is Serine 264. In another embodiment, the Serine 264 residue is mutated to Alanine (S 264 A).

11 Claims, 7 Drawing Sheets

Figure 5.

```
  1 maadgylpdw ledtlsegir qwwklkpgpp ppkpaerhkd dsrglvlpgy kylgpfngld
 61 kgepvneada aalehdkayd rqldsgdnpy lkynhadaef qerlkedtsf ggnlgravfq
121 akkrvleplg lveepvktap gkkrpvehsp vepdsssgtg kagqqparkr lnfgqtgdad
181 svpdpqplgq ppaapsglgt ntmatgsgap madnnegadg vgnssgnwhc dstwmgdrvi
241 ttstrtwalp tynnhlykqi ssqsgasndn hyfgystpwg yfdfnrfhch fsprdwqrli
301 nnnwgfrpkr lnfklfniqv kevtqndgtt tiannltstv qvftdseyql pyvlgsahqg
361 clppfpadvf mvpqygyltl nngsqavgrs sfycleyfps qmlrtgnnft fsytfedvpf
421 hssyahsqsl drlmnplidq ylyylsrtnt psgtttqsrl qfsqagasdi rdqsrnwlpg
481 pcyrqqrvsk tsadnnnsey swtgatkyhl ngrdslvnpg pamashkdde ekffpqsgvl
541 ifgkqgsekt nvdiekvmit deeeirttnp vateqygsvs tnlqrgnrqa atadvntqgv
601 lpgmvwqdrd vylqgpiwak iphtdghfhp splmggfglk hpppqilikn tpvpanpstt
661 fsaakfasfi tqystgqvsv eiewelqken skrwnpeiqy tsnynksvnv dftvdtngvy
721 seprpigtry ltrnl (SEQ. ID. NO.: 1)
```

Figure 6.

```
  1 maadgylpdw ledtlsegir qwwklkpgpp ppkpaerhkd dsrglvlpgy kylgpfngld
 61 kgepvneada aalehdkayd rqldsgdnpy lkynhadaef qerlkedtsf ggnlgravfq
121 akkrvleplg lveepvktap gkkrpvehsp vepdsssgtg kagqqparkr lnfgqtgdad
181 svpdpqplgq ppaapsglgt ntmatgsgap madnnegadg vgnssgnwhc dstwmgdrvi
241 ttstrtwalp tynnhlykqi ssqagasndn hyfgystpwg yfdfnrfhch fsprdwqrli
301 nnnwgfrpkr lnfklfniqv kevtqndgtt tiannltstv qvftdseyql pyvlgsahqg
361 clppfpadvf mvpqygyltl nngsqavgrs sfycleyfps qmlrtgnnft fsytfedvpf
421 hssyahsqsl drlmnplidq ylyylsrtnt psgtttqsrl qfsqagasdi rdqsrnwlpg
481 pcyrqqrvsk tsadnnnsey swtgatkyhl ngrdslvnpg pamashkdde ekffpqsgvl
541 ifgkqgsekt nvdiekvmit deeeirttnp vateqygsvs tnlqrgnrqa atadvntqgv
601 lpgmvwqdrd vylqgpiwak iphtdghfhp splmggfglk hpppqilikn tpvpanpstt
661 fsaakfasfi tqystgqvsv eiewelqken skrwnpeiqy tsnynksvnv dftvdtngvy
721 seprpigtry ltrnl (SEQ. ID. NO.: 2)
```

Figure 7.

```
  1 maadgylpdw ledtlsegir qwwklkpgpp ppkpaerhkd dsrglvlpgy kylgpfngld
 61 kgepvneada aalehdkayd rqldsgdnpy lkynhadaef qerlkedtsf ggnlgravfq
121 akkrvleplg lveepvktap gkkrpvehsp vepdsssgtg kagqqparkr lnfgqtgdad
181 svpdpqplgq ppaapsglgt ntmatgsgap madnnegadg vgnssgnwhc dstwmgdrvi
241 ttstrtwalp tynnhlykqi ssqagaandn hyfgystpwg yfdfnrfhch fsprdwqrli
301 nnnwgfrpkr lnfklfniqv kevtqndgtt tiannltstv qvftdseyql pyvlgsahqg
361 clppfpadvf mvpqygyltl nngsqavgrs sfycleyfps qmlrtgnnft fsytfedvpf
421 hssyahsqsl drlmnplidq ylyylsrtnt psgtttqsrl qfsqagasdi rdqsrnwlpg
481 pcyrqqrvsk tsadnnnsey swtgatkyhl ngrdslvnpg pamashkdde ekffpqsgvl
541 ifgkqgsekt nvdiekvmit deeeirttnp vateqygsvs tnlqrgnrqa atadvntqgv
601 lpgmvwqdrd vylqgpiwak iphtdghfhp splmggfglk hpppqilikn tpvpanpstt
661 fsaakfasfi tqystgqvsv eiewelqken skrwnpeiqy tsnynksvnv dftvdtngvy
721 seprpigtry ltrnl (SEQ. ID. NO.: 3)
```

EFFECTIVE VECTOR PLATFORM FOR GENE TRANSFER AND GENE THERAPY

CROSS-REFERENCE TO RELATED APPLICATIONS

This application is a National Phase of International Application No. PCT/US2010/037239, filed Jun. 3, 2010, which designated the U.S. and that International Application was published under PCT Article 21(2) in English. This application also includes a claim of priority under 35 U.S.C. §119(e) to U.S. provisional patent application No. 61/183,862 filed Jun. 3, 2009.

FIELD OF THE INVENTION

The invention relates generally to the field of virology and genetics, specifically to gene transfer.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Gene transfer vectors based upon the nonpathogenic parvovirus, adeno-associated virus (AAV), have recently emerged as promising tools for therapeutic gene transfer. Due to their relatively low immunogenicity and high transduction efficiency, AAV serotype 2 (AAV2) vectors have advanced to the forefront of human gene therapy. The recombinant AAV virus have been shown to transduce a wide array of cells and tissues in vitro and in vivo[1-5]. The AAV vectors are currently in use in Phase I/II clinical trials for gene therapy of cystic fibrosis, α-1 anti-trypsin deficiency, muscular dystrophy, factor IX-deficiency, and Parkinson's disease[6, 7, 8]. However, some studies suggest that the transduction efficiency of AVV2 vectors in certain tissues types fall short of requirement for adequate level of gene expression[9, 10].

The ubiquitin-proteasome pathway is reported to play an important role in the intracellular trafficking of AAV2 virus[11, 12]. It is reported that AAV2 capsids are phosphorylated at tyrosine residues by the epidermal growth factor receptor (EGFR) tyrosine kinase, but not at serine/threonine residues by casein kinase II (CKII) under cell-free conditions in vitro, and that AVV2 tyrosine-phosphorylation negatively affects viral intracellular trafficking and transgene expression in intact cells in vivo[13]. Recently, it has been reported that mutations of surface-exposed tyrosine residues on AAV2 capsids prevents ubiquitinalation of AAV2 thereby blocking proteasome-mediated degradation leading to generation of high-titer virus that is required for gene therapy[14].

Thus, identification of amino acid motif within a protein sequence such as capsid protein of viruses would be extremely helpful in understanding viral trafficking and its stability in vitro and in vivo systems.

SUMMARY OF THE INVENTION

Various embodiments include a vector, comprising an isolated adeno-associated virus (AAV) capsid comprising one or more mutations that resist ubiquitination. In another embodiment, the one or more mutations that resist ubiquitination comprise an amino acid substitution of a serine residue. In another embodiment, the one or more mutations that resist ubiquitination comprise a Serine 264 Alanine motif. In another embodiment, the one or more mutations that resist ubiquitination comprise an amino acid insertion following amino acid position 264 in an AAV capsid. In another embodiment, the isolated AAV capsid comprises SEQ. ID. NO.: 2. In another embodiment, the isolated AAV capsid comprises SEQ. ID. NO.: 3. In another embodiment, the isolated AAV capsid comprises AAV2. In another embodiment, the isolated AAV capsid comprises AAV8. In another embodiment, the isolated AAV capsid comprises AAV1, AAV3, AAV4, AAV5, AAV6 or AAV7.

Other embodiments include a method of increasing transfection efficiency in an adeno-associated virus (AAV) capsid, comprising providing an AAV capsid, and mutating one or more residues on the AAV capsid to resist ubiquitination. In another embodiment, mutating one or more residues on the AAV capsid to resist ubiquitination comprises inhibition of phosphorytion of one or more AAV capsid serine residues. In another embodiment, mutating one or more residues on the AAV capsid to resist ubiquitination comprises mutating Serine 264 into Alanine. In another embodiment, mutating one or more residues on the AAV capsid to resist ubiquitination comprises inserting an amino acid residue before Serine 264. In another embodiment, the AAV capsid comprises SEQ. ID. NO.: 1, SEQ. ID. NO.: 2 and/or SEQ. ID. NO.: 3. In another embodiment, the AAV capsid comprises AAV2. In another embodiment, the AAV capsid comprises AAV8. In another embodiment, the AAV capsid comprises AAV1, AAV3, AAV4, AAV5, AAV6 or AAV7.

Other embodiments include a method of transfecting a cell, comprising providing an isolated adeno-associated virus (AAV) capsid comprising one or more mutations that resist ubiquitination, and transfecting the cell with the AAV capsid. In another embodiment, the cell is a HeLa and/or HepG2 cell. In another embodiment, the cell is transfected directly. In another embodiment, the one or more mutations that resist ubiquitination comprise an amino acid substitution of a serine residue. In another embodiment, the one or more mutations that resist ubiquitination comprise a Serine 264 Alanine motif. In another embodiment, the one or more mutations that resist ubiquitination comprise an amino acid insertion following amino acid position 264 in an AAV capsid. In another embodiment, the isolated AAV capsid comprises SEQ. ID. NO.: 2. In another embodiment, the isolated AAV capsid comprises SEQ. ID. NO.: 3. In another embodiment, the isolated AAV capsid comprises AAV2. In another embodiment, the isolated AAV capsid comprises AAV8. In another embodiment, the isolated AAV capsid comprises AAV1, AAV3, AAV4, AAV5, AAV6 or AAV7.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 5 depicts, in accordance with an embodiment herein, an example of an AAV amino acid sequence, including the 264 SGAS 267 motif, at amino acid positions 264-267, which has been underlined. The sequence is also described herein as SEQ. ID. NO.: 1.

FIG. 6 depicts, in accordance with an embodiment herein, an example of an AAV amino acid sequence where the Serine residue at position 264 has been substituted with an Alanine residue. The 264 AGAS 267 motif has been underlined. The sequence is also described herein as SEQ. ID. NO.: 2.

FIG. 7 depicts, in accordance with an embodiment herein, an example of an AAV amino acid sequence where the Serine residues at both positions 264 and at 267 has been substituted with Alanine residues. The 264 AGAA 267 motif has been underlined. The sequence is also described herein as SEQ. ID. NO.: 3.

DESCRIPTION OF THE INVENTION

Figure 1:
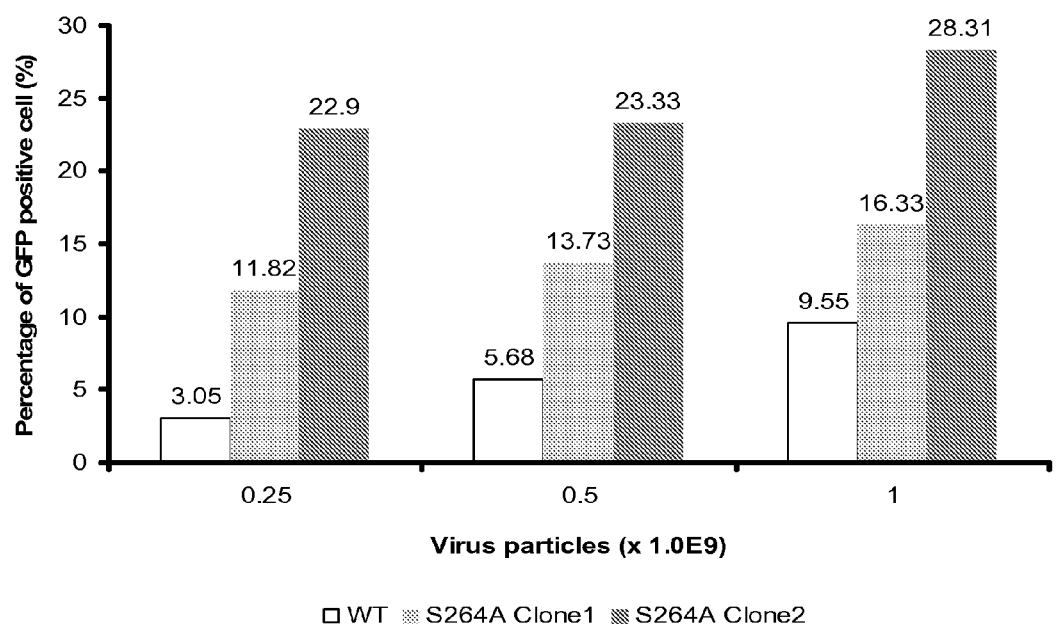
FIG. 1 depicts, in accordance with an embodiment herein, charts of transduction efficiency in HeLa cells. Cells were plated in wells of a 24 well plate with a density of 1.0E5 cells per well. After 16 hours, the cells were transducted with different types of virus with a density of 1.0E9, 0.5E9 and 0.25E9 genomic particles per well. After 48 hours after the cells were transducted, the cells were collected and GFP positive cells were detected with FACS.
Figure 2:
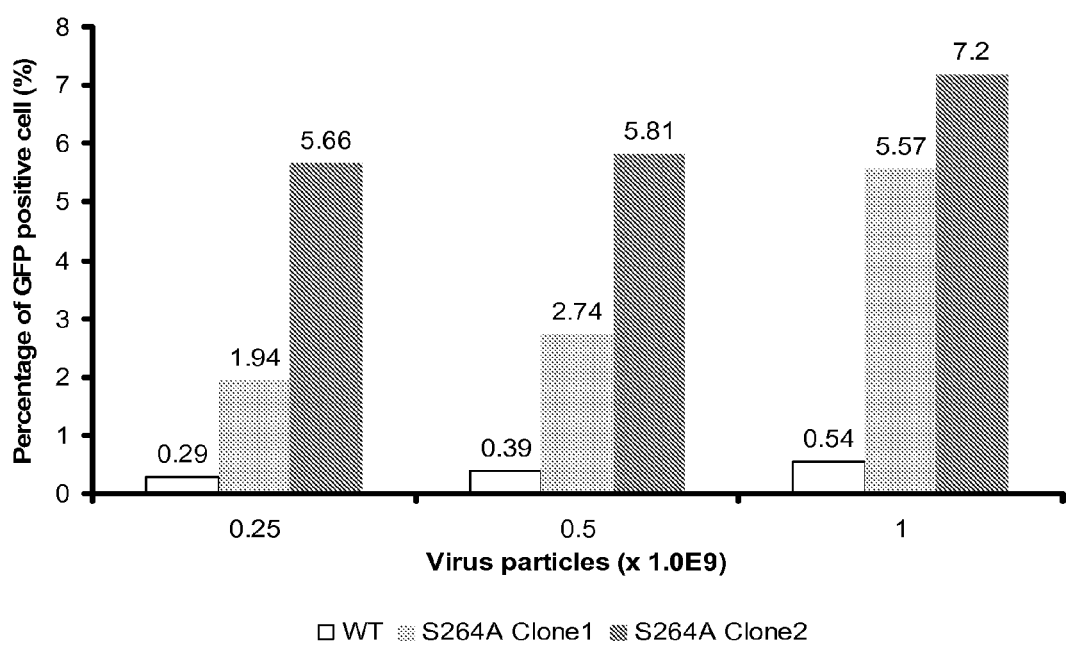
FIG. 2 depicts, in accordance with an embodiment herein, charts of transduction efficiency in HepG2 cells. Cells were plated in wells of a 24 well plate with a density of 1.0E5 cells per well. After 16 hours, the cells were transducted with different types of virus with a density of 1.0E9, 0.5E9 and 0.25E9 genomic particles per well, after transduced 48 hours, cell were collected and GFP positive cells were detected with FACS.
Figure 3:
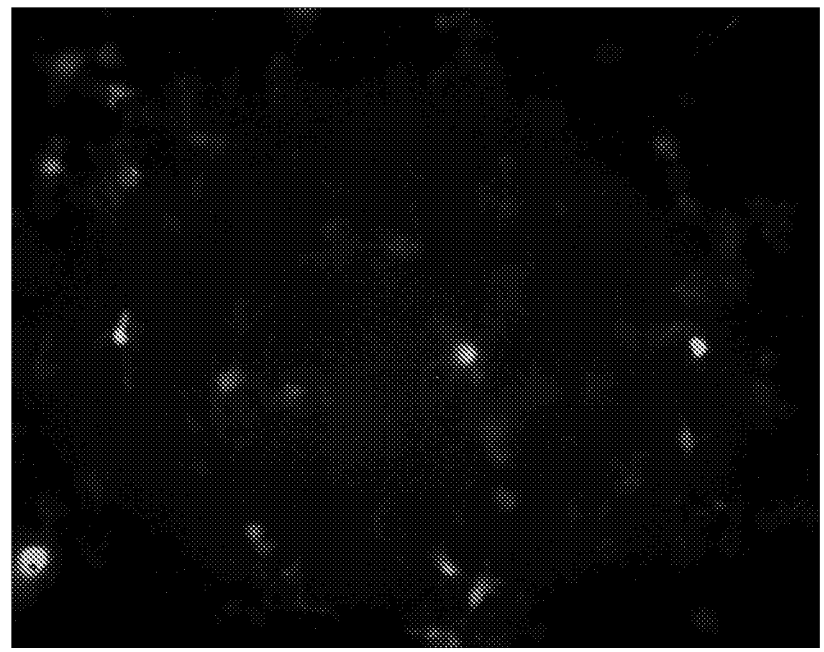
FIG. 3 (a)-(c) depicts, in accordance with an embodiment herein, HepG2 cells, with (a) wild type, (b) S 264 A Clone 1, and (c) S 264 A Clone 2 as viewed as fluorescence microscopy images.
Figure 3:
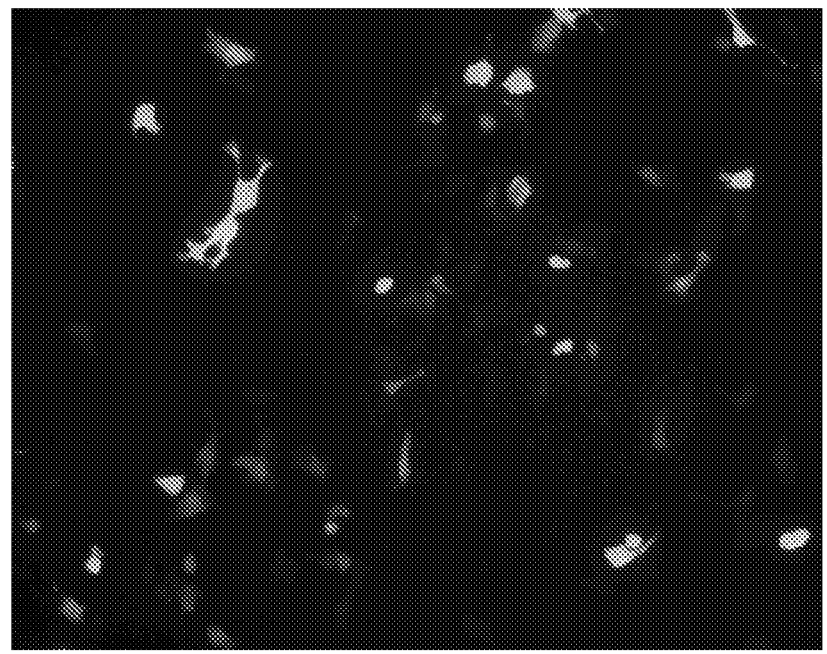
Figure 3:
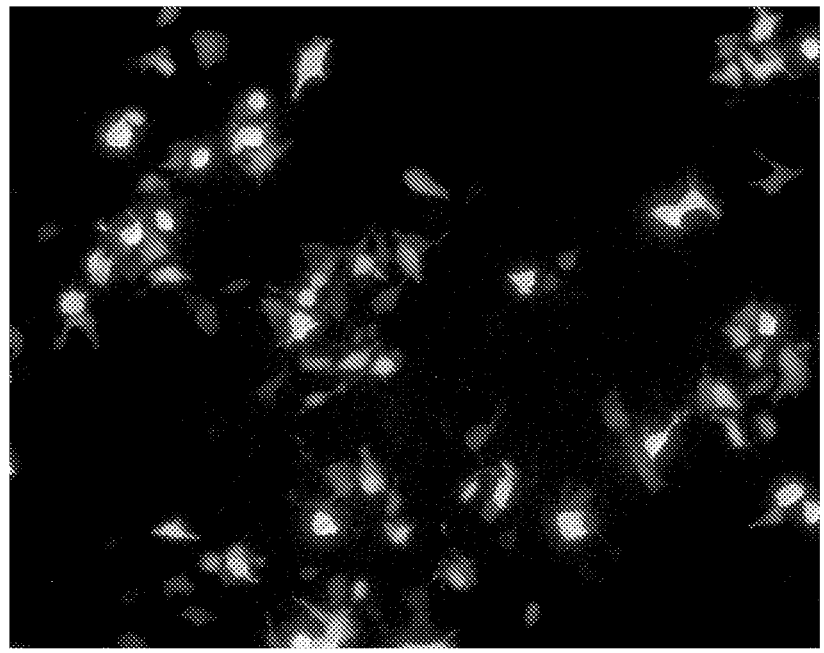
Figure 4:
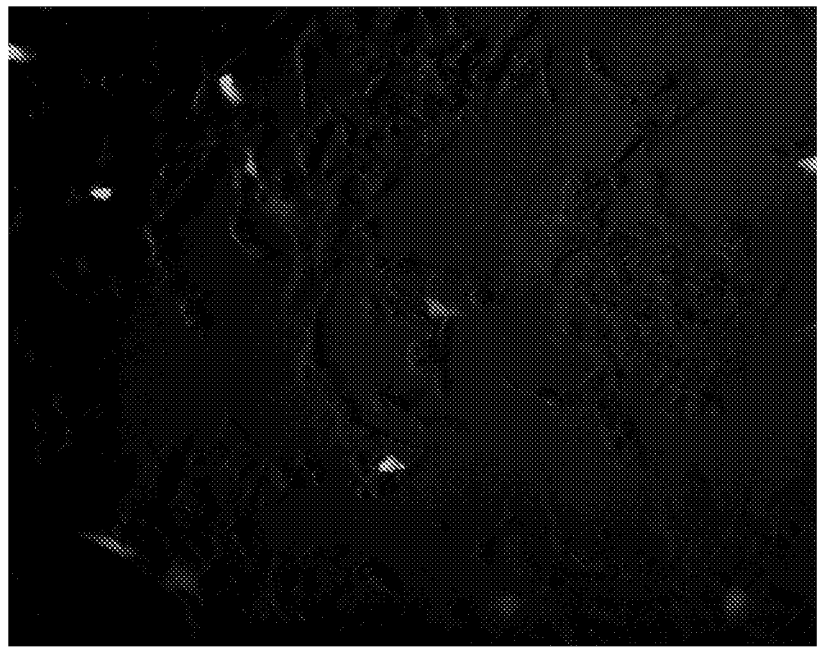
FIG. 4 (a)-(c) depicts, in accordance with an embodiment herein, HeLa cells, with (a) wild type, (b) S 264 A Clone 1, and S 264 A Clone 2 as viewed as fluorescence microscopy images.
Figure 4:
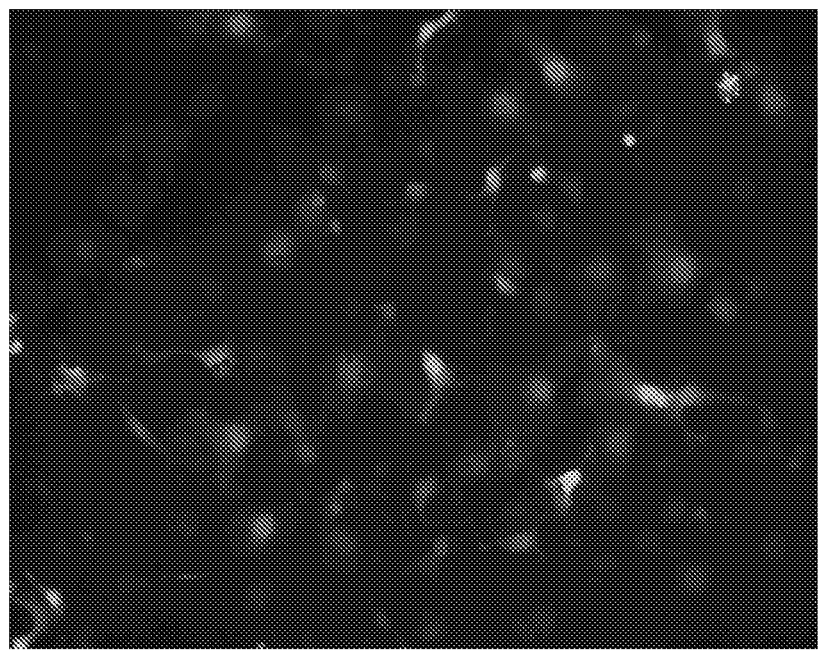
Figure 4:
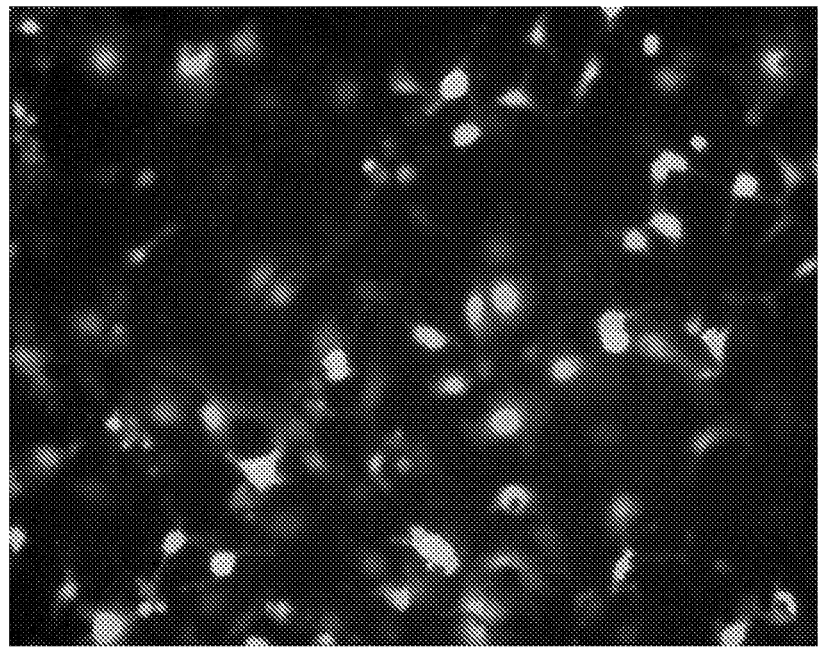

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used herein, "AAV" means adeno-associated virus.

As used herein, "264 SGAS 267" describes a motif of AAV where amino acid positions 264-267 are made up of S, G, A and S amino acids, respectively. The 264 SGAS 267 motif is described herein as SEQ. ID. NO.: 4, as well as SEQ. ID. NO.: 1.

As disclosed herein, the inventors mutated the amino acid Serine 264 into Alanine. The HeLa and HepG2 cells, two cell types that are widely used for the transfection of AAV2 virus was transfected with the mutated virus expressing green florescent protein (GFP) as a reporter gene. Transfection with the wild type AAV2 virus was used for comparison and served as a control. Florescent microscopy image of the transfected cells that were obtained 24 hr after transfection revealed that the wild type AAV2 virus tranfected few cells in both cell types. However, the Serine 264 to Alanine mutated AAV2 virus was considerably more effective in transfecting the two cell types. Flow cytometry analysis of the transfected cells showed that the mutation of the Ser residue at position 264 increased transfection efficiency of the AAV2 virus by more than 7 fold. Together, these data demonstrate that targeting the Ser amino acid motifs within the AAV virus leads to a generation of new AAV virus with significantly greater transfection efficiency than the wild type AAV2 virus. This can have a significant impact on gene therapy approaches by reducing the number of viral particle that need to be injected into a patient to produce therapeutic level of transgene; thus, significantly reducing the side effects and improving the efficiency of gene transfer and gene therapy. Thus, in accordance with an embodiment described herein, Serine 264 to Alanine mutated AAV2 serves as a novel enhanced and safer platform for gene transfer and gene therapy of a variety of diseases and conditions including but not limited to cardiovascular disease.

In one embodiment, the present invention provides a method of improving efficiency of gene transfer and/or gene therapy to a cell by inhibiting phosphorylation of one or more serine residues of a virus capsid protein, where the inhibition of the phosphorylation of one or more serine residues results in a decrease of ubiquitination of the virus capsid protein in the cell. In another embodiment, the decrease of ubiquitination of the capsid protein results in a decrease in proteasome-mediated degradation of the capsid. In another embodiment, the inhibition of the phosphorylation of one or more serine residues is caused by mutating the serine residue. In another embodiment, one of the one or more serine residues is Serine 264. In another embodiment, the Serine 264 residue is mutated to Alanine (S 264 A). In another embodiment, the virus is AAV. In another embodiment, the virus is AAV2.

In another embodiment, the present invention provides a method of performing gene transfer and/or gene therapy by transducing a cell using an AAV2 vector, where the AAV2 vector contains one or more mutated serine residues. In another embodiment, the one or more mutated serine residues prevent ubiquitination of AAV2 and block proteasome-mediated degradation. In another embodiment, the one or more mutated serine residues allows generation of high-titer virus. In another embodiment, the mutated serine residues are at amino acid positions 264 and/or 267 of AAV2.

In various embodiments, the present invention provides biopharmaceutical compositions including a biopharmaceutically acceptable excipient along with a therapeutically effective amount of AAV2 capsids with mutated serine residues. "Biopharmaceutically acceptable excipient" means an excipient that is useful in preparing a biopharmaceutical composition that is generally safe, non-toxic, and desirable, and includes excipients that are acceptable for veterinary use as well as for human biopharmaceutical use. Such excipients may be solid, liquid, semisolid, or, in the case of an aerosol composition, gaseous.

In various embodiments, the biopharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The biopharmaceutical compositions according to the invention can also contain any biopharmaceutically acceptable carrier. "Biopharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "biopharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The biopharmaceutical compositions according to the invention can also be encapsulated, tableted or prepared in an emulsion or syrup for oral administration. Biopharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The biopharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The biopharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the biopharmaceutically acceptable carrier or carriers in the formulation, and the route of administration. One skilled in the clinical and biopharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy(Gennaro ed. 20th edition, Williams & Wilkins PA, USA) (2000).

Typical dosages of an effective AAV2 capsid with one or more mutated serine residues can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Ubiquitination Binding Motifs

Protein ubiquitination regulates protein localization, activity and substrate specificity[15]. Now, protein ubiquitination is considered one of the main regulatory mechanisms in eukaryotic cells and one of the principal roles is to target the half-life of proteins by targeting them for proteasomal degradation[15, 16]. The SCF (Skp1, Cul1 and F-box protein) complex E3 ubiquitin ligases target many proteins including IkBα, β-catenin, and interferon-α receptor for proteolysis in diverse cellular processes, whether receptor tyrosine kinases are also targeted by SCF complex E3 ligases is not known. β-Trcp proteins serve as the substrate recognition subunits for the SCF complexes[15]. To date, two mammalian β-Trcp (β-transducin repeat containing protein) namely β-Trcp1 and β-Trcp2 have been identified[15], although it is not clear whether they have overlapping role or each of them recognizes specific substrates. A recent study indicates that β-Trcp recognizes the doubly phosphorylated DSG motif (DpSG-ΦXpS, where Φ represents a hydrophobic and X represents any amino acid). In addition to the DSG motif, a recent study by Kanemori et al. (2005) indicates that β-Trcp binds to Xenopus Cdc25A via a novel non-phosphorylated binding motif, DDGΦXD[17].

Example 2

Phosphorylation of Serine for Ubiquitination

Based on the sequence homology analysis we recently found that AAV2 capsids contain a motif, $_{264}SGAS_{267}$. While this mutation is not identical to the reported DSG motif, the inventors hypothesized that the amino acid sequence motif is close enough to the sequence motif recognized by the F-box proteins. This suggests that this motif in the AAV2 capsids is recognized by the ubiquitin system leading to the degradation of the virus. The phosphorylation of capsid proteins at Serine residues is required for ubiquitination of intact AAV2 particles and that a substantial number of ubiquitinated virions are recognized and degraded by ubiquitin system leading to inefficient nuclear transport. Therefore, the inventors reasoned that substitution of Serines within the motif will allow the vector to resist ubiquitination and, thus, proteasome-mediated degradation.

Example 3

Serine 264 to Alanine Mutated AAV2

Greater Transfection Efficiency

The inventors mutated the amino acid Serine 264 into Alanine. The HeLa and HepG2 cells, two cell types that are widely used for the transfection of AAV2 virus was transfected with the mutated virus expressing green florescent protein (GFP) as a reporter gene. Transfection with the wild type AAV2 virus was used for comparison and served as a control. Florescent microscopy image of the transfected cells that were obtained 24 hr after transfection revealed that the wild type AAV2 virus tranfected few cells in both cell types. However, the Serine 264 to Alanine mutated AAV2 virus was considerably more effective in transfecting the two cell types. Flow cytometry analysis of the transfected cells showed that the mutation of the Ser residue at position 264 increased transfection efficiency of the AAV2 virus by more than 7 fold. Together, these data demonstrate that targeting the Ser amino acid motifs within the AAV virus leads to a generation of new AAV virus with significantly greater transfection efficiency than the wild type AAV2 virus. This can have a significant impact on gene therapy approaches by reducing the number of viral particle that need to be injected into a patient to produce therapeutic level of transgene; thus, significantly reducing the side effects and improving the efficiency of gene transfer and gene therapy. Thus, in accordance with an embodiment described herein, Serine 264 to Alanine mutated AAV2 serves as a novel enhanced and safer platform for gene transfer and gene therapy of a variety of diseases and conditions including but not limited to cardiovascular disease.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. Muzyczka N. Use of adeno-associated virus as a general transduction vector for mammalian cells. *Curr Top Microbiol Immunol.* 1992; 158:97-129.
2. Podsakoff G, Wong K K, Jr., Chatterjee S. Efficient gene transfer into nondividing cells by adeno-associated virus-based vectors. *J. Virol.* 1994; 68:5656-5666.
3. Flotte T R, Afione S A, Conrad C, McGrath S A, Solow R, Oka H, Zeitlin P L, Guggino W B, Carter B J. Stable in vivo expression of the cystic fibrosis transmembrane conductance regulator with an adeno-associated virus vector. *Proceedings of the National Academy of Sciences of the United States of America.* 1993; 90:10613-10617.
4. Xiao X, Li J, Samulski R J. Efficient long-term gene transfer into muscle tissue of immunocompetent mice by adeno-associated virus vector. *J. Virol.* 1996; 70:8098-8108.
5. Snyder R O, Miao C H, Patijn G A, Spratt S K, Danos O, Nagy D, Gown A M, Winther B, Meuse L, Cohen L K, Thompson A R, Kay M A. Persistent and therapeutic concentrations of human factor IX in mice after hepatic gene transfer of recombinant AAV vectors. *Nat Genet.* 1997; 16:270-276.
6. Flotte T, Carter B, Conrad C, Guggino W, Reynolds T, Rosenstein B, Taylor G, Walden S, Wetzel R. A Phase I Study of an Adeno-Associated Virus-CFTR Gene Vector in Adult CF Patients with Mild Lung Disease. Johns Hopkins Children's Center, Baltimore, Md. *Human Gene Therapy.* 1996; 7:1145-1159.
7. Phase I Trial of Intramuscular Injection of a Recombinant Adeno-Associated Virus Alpha 1-Antitrypsin (rAAV2-CB-hAAT) Gene Vector to AAT-Deficient Adults. *Human Gene Therapy.* 2004; 15:93-128.
8. Kay M A, Manno C S, Ragni M V, Larson P J, Couto L B, McClelland A, Glader B, Chew A J, J Tai S, Herzog R W, Arruda V, Johnson F, Scallan C, Skarsgard E, Flake A W, High K A. Evidence for gene transfer and expression of factor IX in haemophilia B patients treated with an AAV vector. *Nat Genet.* 2000; 24:257-261.
9. Zabner J, Seiler M, Walters R, Kotin R M, Fulgeras W, Davidson B L, Chiorini J A. Adeno-associated virus type 5 (AAV5) but not AAV2 binds to the apical surfaces of airway epithelia and facilitates gene transfer. *J. Virol.* 2000; 74:3852-3858.
10. Thomas C E, Storm T A, Huang Z, Kay M A. Rapid uncoating of vector genomes is the key to efficient liver transduction with pseudotyped adeno-associated virus vectors. *J. Virol.* 2004; 78:3110-3122.
11. Douar A-M, Poulard K, Stockholm D, Danos O. Intracellular Trafficking of Adeno-Associated Virus Vectors: Routing to the Late Endosomal Compartment and Proteasome Degradation. *J. Virol.* 2001; 75: 1824-1833.
12. Ding W, Zhang L N, Yeaman C, Engelhardt J F. rAAV2 Traffics through both the Late and the Recycling Endosomes in a Dose-Dependent Fashion. *Mol Ther.* 2006; 13:671-682.
13. Zhong L, Zhao W, Wu J, Li B, Zolotukhin S, Govindasamy L, Agbandje-McKenna M, Srivastava A. A dual role of EGFR protein tyrosine kinase signaling in ubiquitination of AAV2 capsids and viral second-strand DNA synthesis. *Mol Ther.* 2007; 15:1323-1330.
14. Zhong L, Li B, Mah C S, Govindasamy L, Agbandje-McKenna M, Cooper M, Herzog R W, Zolotukhin I, Warrington K H, Jr., Weigel-Van Aken K A, Hobbs J A, Zolotukhin S, Muzyczka N, Srivastava A. Next generation of adeno-associated virus 2 vectors: point mutations in tyrosines lead to high-efficiency transduction at lower doses. *Proc Natl Acad Sci USA.* 2008; 105:7827-7832.
15. Cardozo T, Pagano M. The SCF ubiquitin ligase: insights into a molecular machine. *Nat Rev Mol Cell Biol.* 2004; 5:739-751.
16. Vaux D L, Silke J. IAPs, RINGS and ubiquitylation. *Nat Rev Mol Cell Biol.* 2005; 6:287-297.
17. Kanemori Y, Uto K, Sagata N. Beta-TrCP recognizes a previously undescribed nonphosphorylated destruction motif in Cdc25A and Cdc25B phosphatases. *Proc Natl Acad Sci USA.* 2005; 102:6279-6284.

The invention claimed is:

1. A vector, comprising:
   an isolated adeno-associated virus (AAV) capsid comprising SEQ. ID. NO.: 2 or SEQ ID NO: 3 that resist ubiquitination.

2. The vector of claim 1, wherein the isolated AAV capsid comprises SEQ. ID. NO.: 2.

3. The vector of claim 1, wherein the isolated AAV capsid comprises SEQ. ID. NO.: 3.

4. A method of increasing transfection efficiency in an adeno-associated virus (AAV) capsid, comprising:
   providing a wild-type AAV2 capsid comprising a Serine Glycine Alanine Serine (SGAS) (SEQ ID NO:4) motif; and
   mutating one or more residues in the SGAS (SEQ ID NO:4) motif on the wild-type AAV2 capsid to resist ubiquitination to result in a AAV2 capsid comprising SEQ. ID. NO.: 2 or SEQ. ID. NO.: 3.

5. The method of claim 4, wherein mutating the one or more residues in the SGAS (SEQ ID NO:4) motif on the AAV capsid results in the AAV capsid comprising SEQ. ID. NO.: 2.

6. A method of transfecting a cell, comprising:
   providing an isolated adeno-associated virus (AAV) capsid comprising SEQ ID NO: 2 or SEQ ID NO:3 that resist ubiquitination; and
   transfecting the cell with the AAV capsid.

7. The method of claim 6, wherein the cell is a HeLa and/or HepG2 cell.

8. The method of claim 6, wherein the cell is transfected directly.

9. The method of claim 6, wherein the isolated AAV capsid comprises SEQ. ID. NO.: 2.

10. The method of claim 6, wherein the isolated AAV capsid comprises SEQ. ID. NO.: 3.

11. The method of claim 4, wherein mutating the one or more residues in the SGAS (SEQ ID NO:4) motif on the AAV capsid results in the AAV capsid comprising SEQ. ID. NO.: 3.

* * * * *

SEQUENCE LISTING

```
<160> NUMBER OF SEQ ID NOS: 4

<210> SEQ ID NO 1
<211> LENGTH: 735
<212> TYPE: PRT
<213> ORGANISM: adeno-associated virus

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175
```

```
Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590
```

```
Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 2
<211> LENGTH: 735
<212> TYPE: PRT
<213> ORGANISM: adeno-associated virus

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240
```

```
Thr Thr Ser Thr Arg Thr Trp Ala Leu Pro Thr Tyr Asn Asn His Leu
            245                 250                 255
Tyr Lys Gln Ile Ser Ser Gln Ala Gly Ala Ser Asn Asp Asn His Tyr
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
        290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
            450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
            530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
        610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
```

-continued

```
Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 3
<211> LENGTH: 735
<212> TYPE: PRT
<213> ORGANISM: adeno-associated virus

<400> SEQUENCE: 3

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ala Gly Ala Ala Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300
```

-continued

```
Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
                610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
                690                 695                 700

Asn Lys Ser Val Asn Val Asp Phe Thr Val Asp Thr Asn Gly Val Tyr
705                 710                 715                 720
```

```
Ser Glu Pro Arg Pro Ile Gly Thr Arg Tyr Leu Thr Arg Asn Leu
                725                 730                 735

<210> SEQ ID NO 4
<211> LENGTH: 4
<212> TYPE: PRT
<213> ORGANISM: adeno-associated virus

<400> SEQUENCE: 4

Ser Gly Ala Ser
1
```